US008511820B2

(12) United States Patent
Trachtman

(10) Patent No.: US 8,511,820 B2
(45) Date of Patent: Aug. 20, 2013

(54) DEVICE TO MEASURE FUNCTIONS OF THE EYE DIRECTLY

(75) Inventor: Joseph N. Trachtman, Seattle, WA (US)

(73) Assignee: Joseph N. Trachtman, Seattle, WA (US)

( * ) Notice: Subject to any disclaimer, the term of this patent is extended or adjusted under 35 U.S.C. 154(b) by 0 days.

(21) Appl. No.: 13/481,218

(22) Filed: May 25, 2012

(65) Prior Publication Data

US 2012/0307204 A1 Dec. 6, 2012

Related U.S. Application Data

(60) Provisional application No. 61/492,130, filed on Jun. 1, 2011.

(51) Int. Cl.
*A61B 3/00* (2006.01)

(52) U.S. Cl.
USPC .......................................... 351/203; 351/246

(58) Field of Classification Search
USPC ................................................ 351/203, 246
See application file for complete search history.

(56) References Cited

U.S. PATENT DOCUMENTS

| | | | | |
|---|---|---|---|---|
| 4,162,828 | A | 7/1979 | Trachtman | |
| 4,533,221 | A | 8/1985 | Trachtman | |
| 4,660,945 | A | 4/1987 | Trachtman | |
| 5,002,384 | A | 3/1991 | Trachtman | |
| 5,306,228 | A | 4/1994 | Rubins | |
| 5,374,193 | A | 12/1994 | Trachtman | |
| 5,518,497 | A | 5/1996 | Widjaja et al. | |
| 5,684,561 | A | 11/1997 | Yancey | |
| 6,631,989 | B2 * | 10/2003 | Odom et al. | 351/205 |
| 7,334,894 | B2 | 2/2008 | Hillis et al. | |
| 7,731,360 | B2 | 6/2010 | MacDougall et al. | |
| 2010/0076253 | A1 | 3/2010 | Altman et al. | |
| 2010/0149073 | A1 | 6/2010 | Chaum et al. | |
| 2011/0054296 | A1 | 3/2011 | McCarthy et al. | |

* cited by examiner

*Primary Examiner* — Jack Dinh
(74) *Attorney, Agent, or Firm* — Lowe Graham Jones PLLC

(57) ABSTRACT

A device for accommodation training includes a primary light and a sensor supported by a housing and configured to be worn atop the head of the user to capture light reflected by the retina. One or more alignment lights may be provided, along with mounts for adjusting the positioning of the lights and sensor. A feedback signal such as an audible tone is produced as a function of the detected light, providing confirmation to the user that a desired control over the ciliary muscle has been achieved.

16 Claims, 5 Drawing Sheets

DEVICE TO MEASURE FUNCTIONS OF THE EYE DIRECTLY

PRIORITY CLAIM

This application claims the benefit of provisional application Ser. No. 61/492,130 filed Jun. 1, 2011, the contents of which are incorporated by reference.

FIELD OF THE INVENTION

This invention relates to devices for use in accommodation training, particularly including devices for facilitating biofeedback using eye refraction to enter an alpha brain wave (ABW) state, and methods for using such devices.

BACKGROUND OF THE INVENTION

Prior systems have sought to provide structures for accommodation training, brainwave training, electromyography training, and dichotic learning through ABW training with a subject's eyes closed. Such systems seek to, for example, reduce nervous tension, decrease reaction time, and otherwise improve physical or athletic performance by training a person to enter an ABW state. Initial ABW training systems required the subject's eyes to be closed, based on the general belief that a person could not enter the ABW state with open eyes. The inventor previously discovered that this belief was in error, and that an ABW state could be achieved with the eyes open and directed to a visual image.

The prior systems have taken advantage of the discovery that accommodation training is an efficient way to accomplish ABW training. In general, accommodation training uses biofeedback to train a patient to improve his or her visual focusing ability. In a typical device, the refraction of the eye is measured and used to produce auditory feedback such as a tone to which the patient may listen. The patient is then trained to be able to control eye focus based on the change in the auditory feedback that is produced as a result of changes in the refraction of the eye. This sort of training program is sometimes known by the general term "accommodation training" Because of the relationship between accommodation training and entry into an ABW state, accommodation training further teaches patients how to enter an ABW state.

An exemplary prior implementation of a system for such training with the subject's eyes open is described in U.S. Pat. No. 5,374,193 by the present inventor, the contents of which are incorporated by reference. The exemplary system was incorporated into a table or stand, thereby requiring the use of a head and chin support or an ophthalmic headband and articulated arm, either of which would seek to hold the patient's head in a fixed position with respect to the table on which the optical system is mounted. While the system was able to allow patients to enter an ABW state, and otherwise engage in accommodation training, the overall system was bulky, awkward for the patient to use, and subject to small head movements. The prior system was also not portable in any realistic sense, requiring patients to travel to a dedicated facility in order to participate in accommodation training.

Additional patents, such as U.S. Pat. Nos. 4,162,828, 4,533,221, 4,660,945, and 5,002,384, measure functions of the eye, such as ocular accommodation and eye position. These references have utilized a system of lenses, mirrors, beam splitters, and double slits. While such prior systems may provide various advantages, they all carry the common disadvantage of requiring a large, bulky, heavy, cumbersome structure that was affected by small head movements.

SUMMARY OF THE INVENTION

The preferred version of the current invention eliminates or reduces the size and complexity of the prior art systems described above, and preferably provides advantages in convenience and portability.

In one version, the system includes a housing for supporting a narrow beam light source, a light sensor, and alignment light sources such as LEDs. A head-mounting structure such as a head band or ear stems such as commonly used with eyeglasses is connected to the housing in order to support the housing on a user's head, with the housing being located closely in front of the user's eyes.

In a preferred version, the system uses an IRLED as the narrow beam light source and a photodiode, CCD, or CMOS component for the sensor.

In one version, the system is configured such that the sensor and IRLED are oriented along alignment paths that are at an angle of six degrees with respect to one another, with the IRLED being positioned one inch from the user's eye, allowing the sensor to measure light from the IRLED as directly reflected from the retina of the eye, and thereby eliminating the need for additional lenses and optical components.

In some versions, pivots, gimbals, or other adjustable connections are provided between the housing and the earpiece, or within the housing, to facilitate adjustment and alignment of the IRLED and sensor with respect to the eye.

In other versions, lenses, mirrors, beam splitters, and double slits can similarly be used to increase sensitivity and precision, although in a much more miniaturized system than described in previous patents. This novel system facilitates making the device mobile, portable, and battery powered, unlike the current bulky and expensive desk top models, which require a head and chin rest. The combination of a head mounted device, and miniaturized optics can be applied to a number of other electro-optical devices utilized in the examination, testing, and training of the human eye.

An additional advantage of the current design allows the thickness of the device to be ⅜" or less making it virtually invisible by the wearer. This allows the wearer to receive training while ambulatory, while being provided with auditory and/or video feedback from portable ear buds or a similar headset.

In some examples, the device is configured to be integrated with a smart phone, notebook computer, tablet computer, portable music player, or computer screen. The feedback may also take the form of a audio or video game in some versions.

While the simplified system is suited for consumer use, slight modifications can make the system suitable for professional use as well as applications other than biofeedback of accommodation. For example, by using an image such as that of a slit there will be a refined retinal image thereby allowing smaller changes and more accurate measurements of the retinal image. Additional techniques such as wavefront refraction can be used to measure the level of accommodation, which would then be converted to a feedback modality (for example, audio or video). An additional advantage of the preferred design allows the thickness of the device to be ⅜" or less making it virtually invisible by the wearer. This allows the wearer to receive training while ambulatory or while being provided with auditory or video feedback from a smart phone or other electronic device in communication with the accommodation training device. The feedback may also take the form of a audio or video game.

These and other features and variations are described in greater detail below, with reference to the accompanying drawings.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

Figure 1:
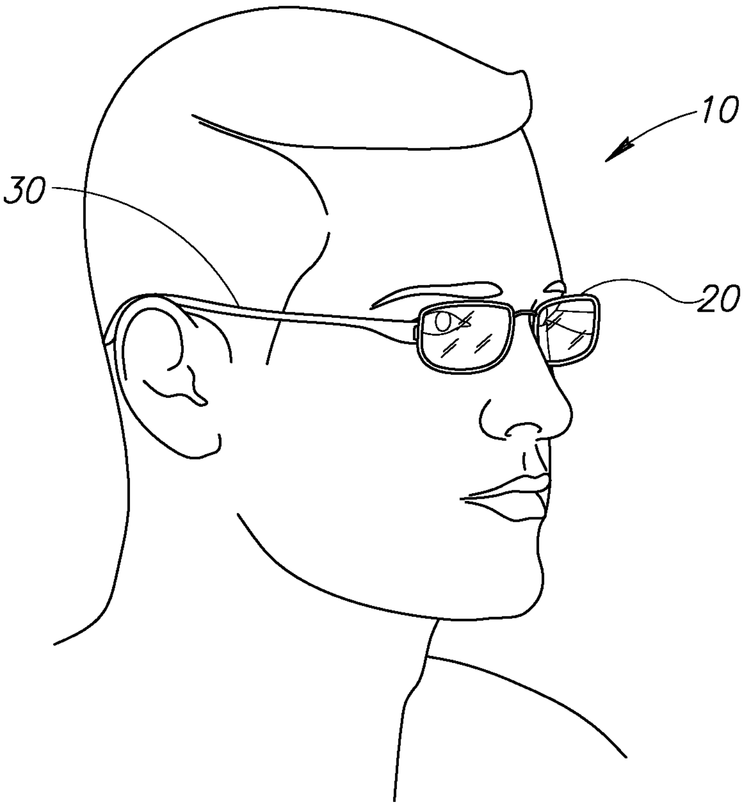
FIG. 1 is an exemplary side view of a version portable accommodation training device, shown being worn by a user.

With reference FIG. 1, a preferred accommodation training device 10 is shown being worn by a user. In this exemplary view, the preferred device is configured to be closely similar to a pair of eyeglasses, sunglasses, or safety glasses. Thus, the preferred version includes an eye-covering portion 20 and an earpiece 30. Most preferably the eye-covering covers both eyes as with the two lenses found in a pair of eyeglasses, and a pair of earpieces with one extending from each lens and being configured to be supported by a user's ear. As shown, the earpieces include a proximal end and a distal end, with the eye-covering portion being carried between the proximal ends of the earpieces.

The eye-covering portion may include actual lenses or similar material covering the eye, thereby giving the device an overall look that is similar to a pair of eyeglasses. Alternatively, the eye-covering portion may be configured as a housing for supporting the electronic components as described below, without also including a lens or the like. In this sense, the "eye-covering portion" does not necessarily cover the entire eye, but rather provides a means for supporting the light and sensor in front of the eye at a desired location. Similarly, the earpiece 30 may take the form of an ear stem or earpiece as with a pair of eyeglasses, or may more generally be configured as a headband or other support structure capable of holding the electronics components in position at a desired location and distance in front of the user's eyes. Thus, in general, a head support mount is provided, with the head support mount being configured as a headband, ear stems, or other structures.

Figure 2:
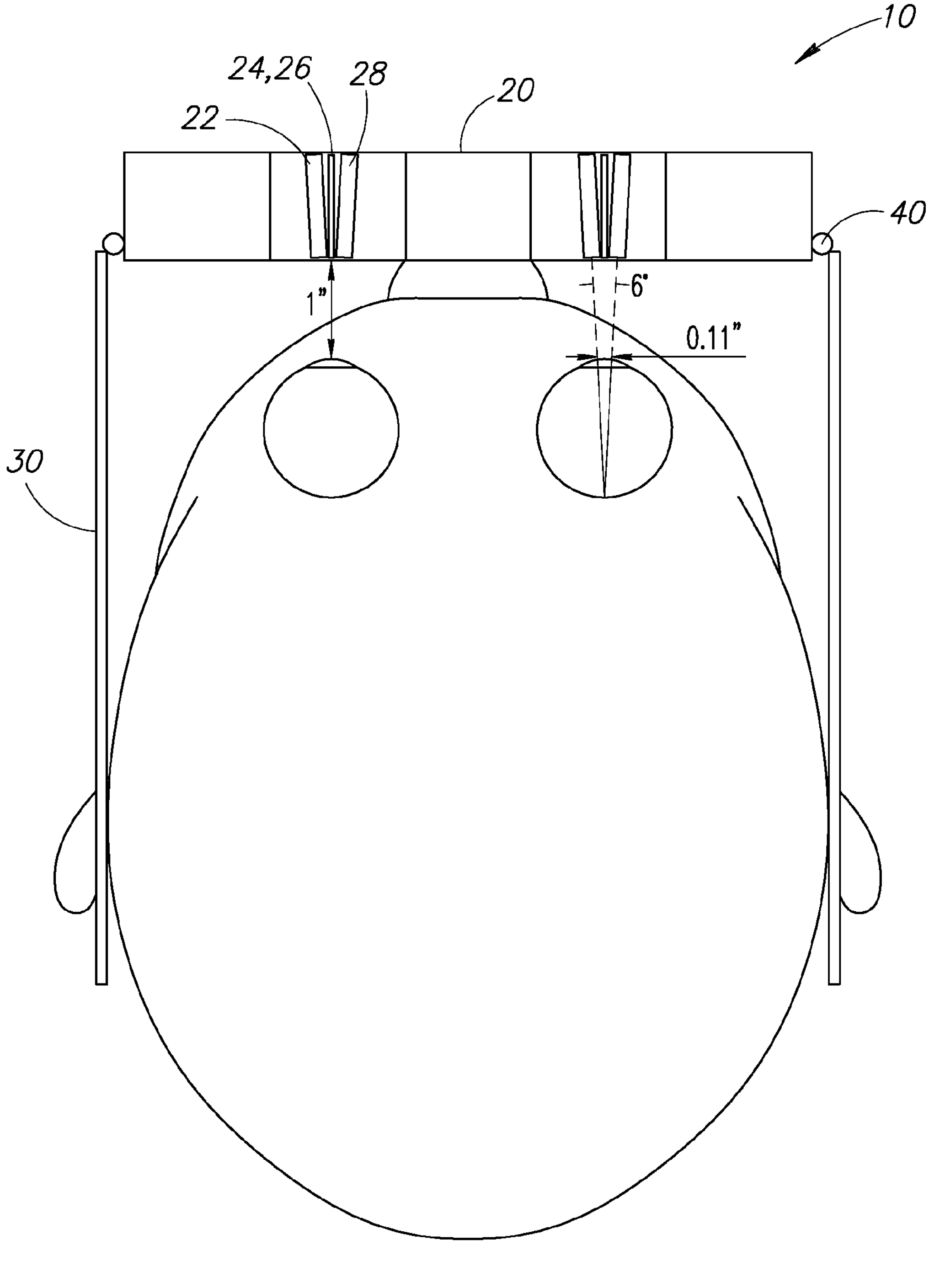
FIG. 2 is a top view of a preferred accommodation training, including representative indications for preferred dimensions and distances.

FIG. 2 provides a top view of a representation of a preferred device, showing the placement and preferred dimensional attributes of the accommodation device as positioned in front of the user's eyes. As shown, the device 10 includes an eye-covering portion 20 and a support or earpiece 30. As illustrated, the eye-covering portion covers both eyes and is of a uniform dimensional thickness between the earpieces. In other versions, such as discussed below, the eye-covering portion may be more similar to traditional classes and carry the other components on an inside surface of the lenses. The eye-covering portion includes several components that are positioned in front of the eye. In some versions the device may be configured with such components arranged in front of only one eye, although in the illustrated version there are separate sets of such components, with one set positioned on the eye-covering portion in front of each eye.

In general, the eye-covering portion includes a pair of housings, each formed to be positioned in front of a respective one of a user's eyes when in use with the device mounted on the user's head. The housings support respective groupings of alignment lights 24, 26, a primary light 22, and a sensor 28.

In a preferred implementation, the primary light 22 is light emitting diode (LED). A particular preferred component is a high powered GaAlAs Infrared LED, such as the Hamamatsu L2690 series, having a narrow beam of radiant output, less than 10 degrees. Other IRLEDs, which have a collimated beam, such as the Hamamatsu L9437, are similarly suited for this application. By using a narrow beam or a collimated beam, the need for collimating lenses (such as used in prior art systems) is eliminated, thereby allowing parallel light to directly enter the pupil of the eye.

In the preferred version the sensor 28 may be a sensor for receiving light reflected after originating from the primary light 22, such as a sensor manufactured by Advanced Photonix, Inc. under model number PDB-C142. Because the sensor has corresponding infra-red sensitivity to the IRLED, it can be used to directly measure the light reflecting from the retina of the eye when the primary light and sensor are both positioned at appropriate distances and angles such that the sensor is in the field of view of the reflected light. While a particular sensor is described above, other components such as a photodiode, CCD (a linear array, a two dimensional matrix, a circular CCD, or a three dimensional CCD), or CMOS with a similar spectral response and sensitivity can be used. While infra-red light is preferable because it is invisible to the eye, visible light sources as well as visible light sensors can be used in other versions of the invention.

As best seen in FIG. 2, the device is configured such that the primary light and sensor are aligned to allow the sensor to receive light reflected from the retina of a user's eyes when the device is worn and in use. As shown, the combination of the dimensions of the earpieces 30 and the configuration of the eye-covering piece 20 and associated mounts provides for a distance of one inch between the front surface of the user's eye (that is, the apex of the cornea) and the light emission surface from the primary light 22. The primary light 22 and sensor 28 are also positioned at an angle of six degrees with respect to one another, providing a separation of 0.11 inches between the entering and exiting light at the apex of the cornea.

In the preferred version there is a six degree angle based on the one inch distance from the eye and the proximity of the IRLED and the photodiode adjacent one another. In alternate versions it is possible to move the IRLED and photodiode apart from one another somewhat, thereby increasing the intersection angle accordingly. It is also possible to increase the distance from the eye, although at about 1 inch the performance is believed to be optimal. Within these variables a mix of dimensions and ranges is possible to produce preferred structures, including most preferably a distance of at least a half inch and less than two inches from the eye, and an angle of at least 4 degrees and less than 10 degrees between the IRLED and photodiode. Likewise, within these dimensional parameters it is possible to produce an accommodation primary device in which the entirety of the device can be provided in a compact fashion and entirely supported by the head of the user.

Figure 3:
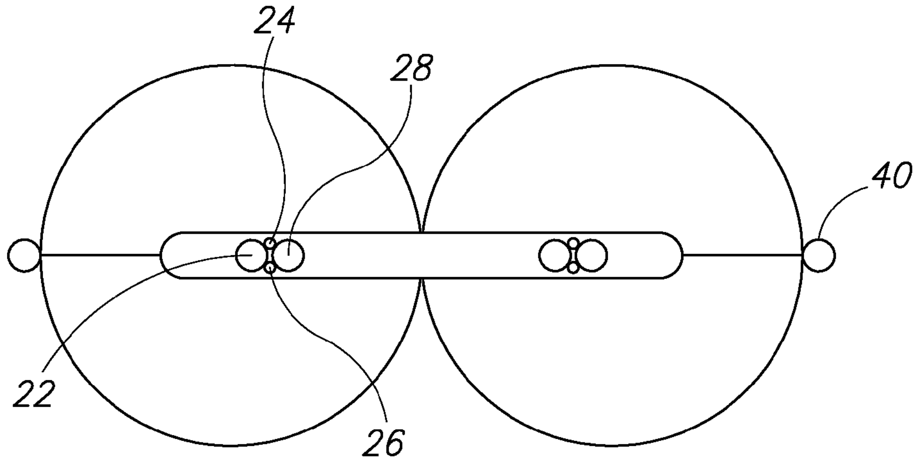
FIG. 3 is a back view of a preferred accommodation training device, showing a perspective as seen by a user wearing a preferred device.

As seen in FIG. 2, one or more alignments lights 24, 26 are also mounted in the housing. In the preferred configuration there are two alignments lights, which in one version are in the form of green LED's. Fiber optic cables (preferably at 3 mm in diameter) are supported by the eye-covering housing and illuminated by the green LEDs. With reference to FIG. 3, in one version a pair of alignment lights are used, with one positioned above the other. In one version, a first alignment light 24 is positioned 0.5 inches above a second alignment light 26. Most preferably the alignment lights are also positioned so that they are not equidistant from the front surface of the user's eyes. In one example, a first LED is positioned to emit light from a distance of one inch from the user's eye while the second LED is positioned to emit light from a distance of 1.5 inches from the user's eye, thereby allowing the use of parallax to achieve alignment between the two LEDs.

One or more gimbals 40 may be provided in order to allow the user to adjust the position of the housing or eye-covering portions with respect to the user's eyes. As illustrated in FIGS. 2 and 3, the gimbals 40 may be positioned between the earpieces and the eye-covering portions, allowing for multiple degree of freedom movement of the eye-covering portions and housings with respect to the user's eyes.

Figure 4:
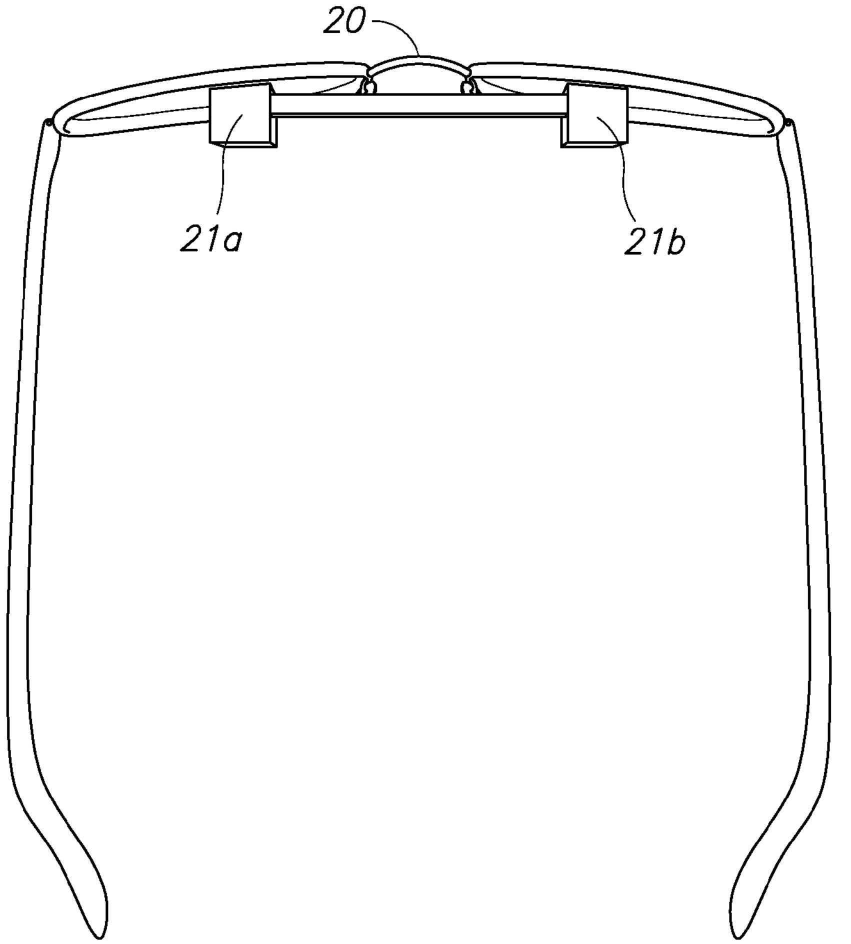
FIG. 4 is a perspective view of an alternate version of a preferred accommodation training device.

In other versions of the invention, the earpieces (or other head support or mount) may be attached to the eye covering portions without gimbals or similar adjustable features. Instead, the one or more housings carrying the lights and sensor may be mounted with alignment features allowing for motion and alignment with respect to the user's eyes. As shown in FIG. 4, the housing may be mounted to the eye-covering portion 20 so that it is positioned between the user's eyes and the eye-covering portion when in use. In this configuration, the housing may be in the form of a single unified housing, or may comprise separate housing sub-structures 21*a*, 21*b*, with one of each of the separate structures being positioned in front of each eye. The housing in this configuration may be mounted to be movable with respect to the eye-covering portion (laterally, pivotally, and up and down), either with both sub-structures 21*a*, 21*b* moveable together, or with each of them independently moveable.

In one version, the housing is attached to a translation stage, which has a thumb screw to achieve alignment, in which rotation of the thumb screw moves the housing in a lateral direction (left or right) with respect to the user's eyes. Pivoting ear pieces allow up and down, and fore-aft adjustment, thereby providing alignment in a left-right direction by the thumb screws, and in an up-down and fore-aft direction by the pivoting ear pieces.

Figure 5:
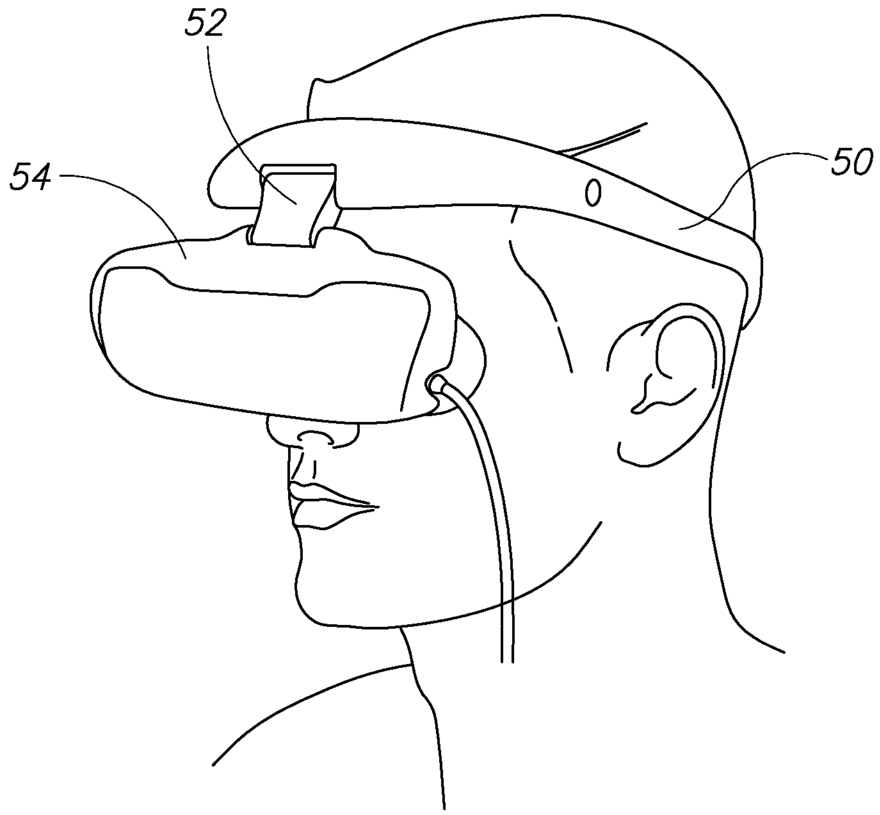
FIG. 5 is a top view of an alternate version of a preferred accommodation training device.

While FIGS. 1-4 illustrate a version in which the accommodation device has a general support structure similar to a typical pair of eyeglasses, in an alternate version the device may include a headband 50 that fully or partially encircles the user's head, with a unified housing 54 for supporting the lights and sensor as described above. In this exemplary version, as shown in FIG. 5, the housing is supported by the headband by a gimbal or other configurable connection point 52 allowing for multiple degrees of freedom to accommodate alignment. The various versions of supports and eye-covering portions as described above may be varied in any fashion. For example, the earpiece may take the form of the headband as illustrated in FIG. 6, but combined with an eye-covering portion similar to traditional eyeglasses as illustrated in FIG. 1.

Figure 6:
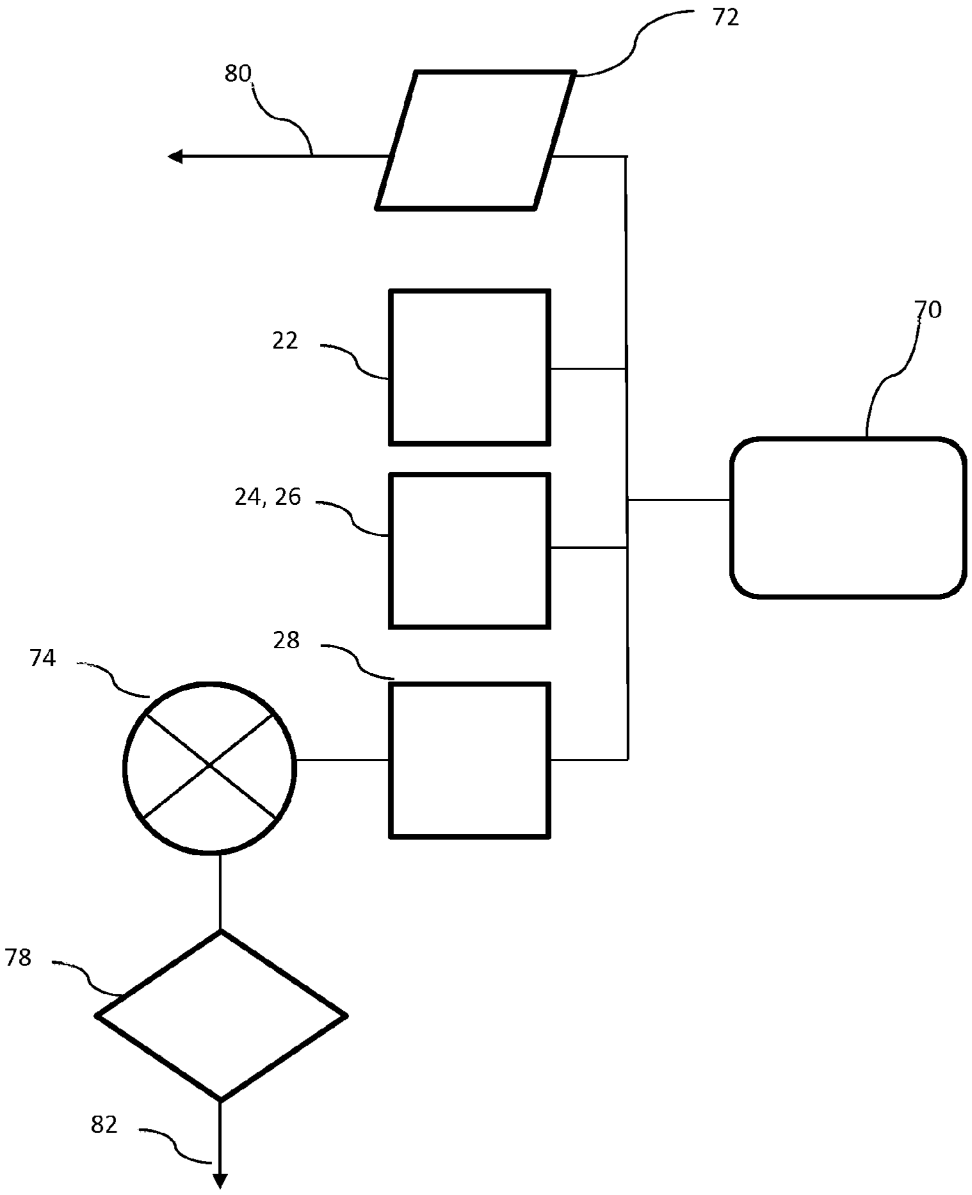
FIG. 6 is a block diagram of a preferred accommodation training device.

FIG. 6 is a block diagram illustrating the components of the preferred device. As shown, the device includes a power supply 70, preferably in the form of a small button battery. In other versions, the power may be provided by a USB or other DC source, including from a computer or other source. The power supply provides power to the alignment lights 24, 26, primary light 22, and sensor 28. It further powers a coprocessor in some versions of the invention, such as may be provided to enable communication with a portable computer, tablet, smart phone, or other device. In such cases, the primary light may be controlled by the signals received from the external device, and likewise the external device may receive a signal representative of the signal received by the photosensor 28 for further processing. The sensor 28 may optionally be in signal communication with a converter 74 for converting the received visual signal to a frequency-based signal for auditory biofeedback. In turn, the converter is in communication with an amplifier to produce an output signal of a desired magnitude. A resulting output signal 82 is provided to a speaker (not shown) which may be an actual speaker mounted on the device or a jack or wire carried on the device 10 for connection to a user's headphones or for input to a portable device such as a smart phone or portable music player. In each case the connections to external devices may be wired or wireless, and may be directly to such devices (such as by a Bluetooth format) or indirectly (such as through a Wi-Fi format).

The IR light from the IRLED enters the pupil of the eye, and the circular image of the IRLED is reflected off the retina of the eye. The reflection from the retina is then imaged onto the photodiode. The distance from the light to the eye is approximately one inch. The photodiode converts the intensity of the light reflected from the retina into a voltage. This output voltage is them feed into a voltage-to-frequency converter (VFC).

For the purposes of accommodation training, the peak voltage received by the sensor is the most significant component. As described above, this peak voltage is used to establish the frequency (or pitch) of an audio tone in one version of audio biofeedback presented to the user through a speaker. Likewise, as noted above, the speaker may be mounted to the accommodation training device, or may be provided to a separate speaker (such as headphones or through a smart phone) through a wired or wireless connection.

In use, the device is placed atop the user's head such that the lights and sensor are positioned in front of the eye or eyes. As a first step, the device is aligned using the alignment lights. In the event the device is improperly aligned when first positioned, the circular alignment lights will appear to be cropped in some fashion, with a portion of the lights being blocked. The user will then move the housing (up, down, left, right, in, or out) as may be necessary to properly align the device such that circular alignment lights are visible.

After the device is aligned, the output provides auditory biofeedback as a function of the light received by the sensor. More specifically, as the ciliary muscle changes the refractive power of the crystalline lens, the retinal image will vary its focus. As the ciliary muscle relaxes, the crystalline lens has a reduced refractive power, and as the ciliary muscle contracts, the crystalline lens has an increased refractive power. This control of the ciliary muscle by the user thereby changes the refraction of the primary light, resulting in a differing magnitude of light received by the sensor. Thus, the user can control the amount of light that is received by the sensor by contracting and relaxing the ciliary muscle. Audible feedback is provided at the output 82 of the device, thereby providing feedback to the user that the user is successfully contracting or relaxing the ciliary muscle. In a preferred version as described above, the output signal changes in frequency as a function of the changes in light intensity received, and therefore the user will hear a sound having a correspondingly high or low frequency as feedback. In other versions of the invention alternate forms of feedback may be used, such as providing a louder and quieter auditory feedback, or providing different types of sounds to indicate contracting and relaxing.

The purpose of the training is for the subject to relax the ciliary muscle, which makes a clearer retinal image. Because a relaxed ciliary muscle is related to an increased ABW, general muscle relaxation, and peripheral increase in temperature, one goal of the training is to teach an increased relaxation of the ciliary muscle.

The measurement of the retinal image is achieved as described above by positioning the angle between the IRLED and the photodiode at six degrees, thereby allowing light to enter the pupil of the eye, reflect from the cornea, and imaged on the photodiode, all without the use of lenses, beam splitters, mirrors, or slits that are bulky and require precise mounting on a fixed and heavy platform. The entire accommodation training device is therefore lightweight and portable, allowing for accommodation training at home or in any facility rather than being restricted to specialized installations with bulky mirrors and lenses that must be carefully and rigidly mounted to heavy platforms.

In the current configuration, as described above, the device can measure ocular accommodation for utilization in a biofeedback device. A primary purpose of the current device is to teach a person how to attain an enhanced ABW state with the eyes open, as described in the inventor's prior U.S. Pat. No. 5,374,193. By using the above described configuration, ABW training can be readily performed using a light-weight, portable, mobile, battery powered device to improve vision functions, concentration, and relaxation with or without the ability to measure EEG and/or EMG and/or finger temperature (as a measure of general relaxation), and/or other physiological functions. Additional purposes of the current device can allow biofeedback of ocular accommodation or other ocular functions, or measurement of such parameters.

The above accommodation device has further been found to be useful to address several physiological issues. As part of a method for addressing such issues, a user is first identified as having a condition or physical issue that may benefit from accommodation training. Such issues may include visual issues (such as acuity, depth perception, color detection, or issues with the visual field of view); a desire to improve reaction times; difficulty in concentration or relaxation; post-traumatic stress disorder; or other nervous-system related issues, such as tinnitus.

Once identified with an area that may be improved through accommodation training, the user then begins a training regimen as described above by first placing the device on the user's head and aligning it properly. Then the user relaxes and contracts the ciliary muscle to achieve a desired auditory feedback (such as tone, volume or other aspects) that indicates achievement of the desired muscular control. In one process, the user practices (for example) making the auditory feedback achieve a higher frequency and then a lower frequency, repeating for a desired number of cycles. Thus, the accommodation of the eye is monitored during this process while providing a biofeedback signal to the user to indicate changes in eye accommodation. The user may then rest for a period and then repeat the cycles of high and low frequencies. Alternatively, the user may work to achieve a high frequency auditory feedback for a period of time, then relax to allow the auditory feedback to drop in frequency for a rest period before repeating the cycle again. Alternate cycle patterns are also possible, providing feedback to the user as the user learns to control the contracting and relaxing of the ciliary muscle.

As described above, the current device teaches users how to achieve an ABW state with their eyes open, and may be used in combination with other biofeedback devices such as for: EEG, EMG, temperature, pulse rate, blood pressure, GSR, heart rate variability, and respiration.

The scope of the invention is not limited by the disclosure of the preferred embodiments as described above. Instead, the invention should be determined entirely by reference to the claims that follow.

The embodiments of the invention in which an exclusive property or privilege is claimed are defined as follows:

1. An accommodation training device, comprising:

an eye-covering portion, the eye-covering portion having a primary light and a sensor; and a head support mount attached to the eye-covering portion and configured to attach the accommodation training device to a user's head such that the accommodation training device is supported by the user's head;

wherein the eye-covering portion is positioned in front of the user's eye with the primary light and sensor directed toward the user's eye when the accommodation training device is attached to the user's head, the eye-covering portion further comprising an alignment light directed toward the user's eye when the accommodation training device is attached to the user's head;

wherein the head support mount and the eye-covering portion are configured such that when the accommodation training device is attached to the user's head the primary light and the sensor are each positioned between 0.5 inches and 2 inches from an apex of a cornea of the user's eye, the primary light and sensor further being aligned with respect to one another to define an intersection angle; and wherein the head support mount and the eye-covering portion are configured such that when the accommodation training device is attached to the user's head the primary light and the sensor are each positioned one inch from the apex of the cornea of the user's eye, and further wherein the intersection angle is six degrees.

2. The accommodation training device of claim 1, wherein the alignment light further comprises a first alignment light and a second alignment light, the first alignment light and the second alignment light being positioned between the training light and the sensor.

3. The accommodation training device of claim 2, wherein the first alignment light is positioned above the second alignment light when the accommodation training device is in position attached to the user's head, the first alignment light further being positioned relatively closer to the user's eye than the second alignment light.

4. The accommodation training device of claim 1, wherein the primary light emits light in the infrared spectrum.

5. The accommodation training device of claim 1, wherein the eye-covering portion is pivotally mounted to the head support mount.

6. The accommodation training device of claim 1, wherein the eye-covering portion is laterally adjustable with respect to the head support mount.

7. The accommodation training device of claim 1, further comprising an output in communication with the sensor, the output configured to provide feedback to the user as a function of a quantity of light received by the sensor.

8. The accommodation training device of claim 7, wherein the output comprises a jack for connection to an audio cable, and further wherein the feedback comprises an auditory signal related to the quantity of light received by the sensor.

9. The accommodation training device of claim 7, wherein the output comprises a means for providing a feedback sound to a speaker.

10. The accommodation training device of claim 1, further comprising a coprocessor, the coprocessor configured for communication with an external electronic device.

11. The accommodation training device of claim 10, wherein the external electronic device is a smart phone.

12. A method for treatment, comprising:

providing an accommodation training device in accordance with claim 1;

attaching the accommodation training device to the head of the user;

monitoring the accommodation of an eye which is undergoing training; and presenting a feedback representative of the accommodation of the eye.

13. The method of claim 12, further comprising determining a condition of the user to be treated by accommodation training, the condition comprising one or more of visual acuity, contrast sensitivity, depth perception, or color perception.

14. The method of claim 12, further comprising determining a condition of the user to be treated by accommodation training, the condition comprising one or more of reaction time, concentration, relaxation, or post-traumatic stress disorder.

15. The method of claim 12, further comprising determining a condition of the user to be treated by accommodation training, the condition comprising tinnitus or other physiological process relating to the autonomic nervous system.

16. An accommodation training device, comprising:

a support having a first earpiece and a second earpiece, each of the first earpiece and the second earpiece having a proximal end and a distal end;

a housing carried between the proximal end of the first earpiece and the proximal end of the second earpiece;

a primary light mounted to the housing and configured to direct light into a space between the distal end of the first earpiece and the distal end of the second earpiece;

a sensor mounted to the housing and configured to detect reflected light originating from the primary light;

an alignment light supported by the housing and directed toward the user's eye when the accommodation training device is attached to the user's head;

the support being configured to attach the accommodation training device to a user's head such that the accommodation training device is supported by the user's head;

wherein the housing is positioned in front of the user's eye with the primary light and the sensor directed toward an eye of the user when the accommodation training device is attached to the user's head; and wherein the support and the housing are configured such that when the accommodation training device is attached to the user's head the primary light and the sensor are each positioned between 0.5 inches and 2 inches from an apex of a cornea of the user's eye, the primary light and sensor further being aligned with respect to one another to define an intersection angle;

wherein the support and the housing portion are configured such that when the accommodation training device is attached to the user's head the primary light and the sensor are each positioned one inch from the apex of the cornea of the user's eye, and further wherein the intersection angle is six degrees.

* * * * *